(12) United States Patent
Wang

(10) Patent No.: US 6,815,528 B2
(45) Date of Patent: Nov. 9, 2004

(54) ORGANIC ELECTROCHROMIC MATERIALS FOR OPTICAL ATTENUATION IN THE NEAR INFRARED REGION

(75) Inventor: Zhi Yuan Wang, Ottawa (CA)

(73) Assignee: TWLinks Inc., Ottawa (CA)

( * ) Notice: Subject to any disclaimer, the term of this patent is extended or adjusted under 35 U.S.C. 154(b) by 56 days.

(21) Appl. No.: 10/151,891

(22) Filed: May 22, 2002

(65) Prior Publication Data

US 2003/0066989 A1 Apr. 10, 2003

Related U.S. Application Data

(60) Provisional application No. 60/292,959, filed on May 24, 2001.

(30) Foreign Application Priority Data

May 24, 2001 (CA) .............................. 2348288

(51) Int. Cl.[7] .............................................. C08G 79/00
(52) U.S. Cl. ...................... 528/395; 528/422; 528/423; 528/425; 528/44; 528/52; 528/55; 252/582
(58) Field of Search ................................ 528/395, 422, 528/423, 425, 44, 52, 55; 252/582

(56) References Cited

U.S. PATENT DOCUMENTS

| 4,978,786 A | 12/1990 | Messina et al. |
| 2002/0067905 A1 | 6/2002 | MacPherson et al. |

OTHER PUBLICATIONS

B. Barber, C. R. Giles, V. Askyuk, R. Ruel, L. Stulzi, D. Bishop, *IEEE Photonics Techno. Lettr*, 10, 1262 (1998).

T. Kawai, M. Koga, M. Okuno, T. Kitoh, *Electron. Lett.*, 34, 264 (1998).

Y.-S. Jin, S.-S. Lee, Y.-S. Son, *Electron. Lett.*, 35, 916 (1998).

N. A. O'Brien, E. R. Mathew, B. P. Hichwa, *OFC 1999*, PD26–I.

M. A. Cowin, R. Varrazza, C. Morgan, R. V. Penty, I. H. White, A. M. McDonagh, S. Bayly, J. Riley, M. D. Ward. J. A. McCleverty, *OFC 2001*, WR6–1.

N. C. Harden, E. R. Humphrey, J. C. Jeffery, S. M. Lee, M. Marcaccio, J. A. McCleverty, L. H. Rees, M. D. Ward, *J. Chem. Soc., Dalton Trans.*, 2417 (1999).

V. Kasack, W. Kaim, H. Binder, J. Jordanov, E. Roth. *Inorg. Chem.*, 34, 1924, (1995).

B. Sullivan, D. Salmon, T. Meyer, *Inorg. Chem.* 17, 3334 (1978).

*Primary Examiner*—Duc Truong
(74) *Attorney, Agent, or Firm*—Blake, Cassels & Graydon LLP; George E. Fisk

(57) ABSTRACT

The invention provides generally a new type of organic electrochromic Near Infrared (NIR)-active materials capable of absorbing and attenuating the light in the NIR region around 1550 nm and forming thin films on electrodes for variable optical attenuator (VOA) applications. They have utility in planar VOA devices. The materials are ruthenium complexes. Unsymmetrical complexes having two different substituents are disclosed, where one substituent is more electron-donating than the other. Complexes which are dimers or trimers (symmetrical or unsymmetrical) are disclosed, as are polymeric complexes. Crosslinked polymeric complex films are also disclosed.

7 Claims, 3 Drawing Sheets

ORGANIC ELECTROCHROMIC MATERIALS FOR OPTICAL ATTENUATION IN THE NEAR INFRARED REGION

This application claims the benefit of provisional application No. 60/292,959 filed on May 24, 2001.

BACKGROUND OF THE INVENTION

A variable optical attenuator (VOA) is an essential component in advanced wavelength division multiplexing (WDM) telecommunication systems, which is used to adjust power variations caused by changes in source power, amplifier gain and other components. Commercially available VOA devices are mainly based on optomechanical and thermo-optic (TO) systems and usually have response times of the order of milliseconds. VOA devices based on MEMS (microelectromechanical system)[1] and TO silica[2] and polymer[3] have been reported. Both TO silica and polymers are also used in development of multi-channel planar VOA devices.

Organic and polymeric materials with desired optical properties, such as electrochromism, are deemed to be commercially useful in planar VOA devices and other integrated photonic devices. Although many electrochromic (EC) materials, including inorganic oxide (e.g., tungsten oxide), organic dye and conducting polymers (e.g., FC: polythiophene), are known to undergo color changes in the visible region (e.g., 300–800 nm) and have potential applications in smart windows and information displays, organic materials that are electrochemically active and electrochromic in the near infrared (NIR) region or specifically within the range of the communication wavelengths (e.g., 1300–1700 nm) are less known. The application of EC materials in VOA has received very limited attention. [4]

The early work by Kaim et al. teaches that the ruthenium (Ru)-complexes of the formula (I):

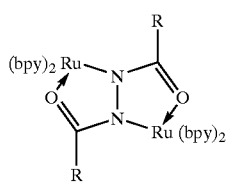

I with 2,2'-bipyridine (bpy) and symmetric azodicarbonyl (ADC) ligands with two identical R groups are electrochromic in the NR region.[5] The ADC-Ru complexes prepared by Kaim.have R groups which are ethoxy ($OCH_2CH_3$), benzoxy ($OCH_2Ph$), methyl ($CH_3$), phenyl (Ph), 4-carboxyphenyl (PhCOOH-4) and 4-methyl benzoate ($PhCOOCH_3$-4).

When in the $Ru^{2+}/Ru^{3+}$ oxidization state, these compounds absorb strongly around 1550 nm. For example, two compounds with R=$CH_3$ and Ph show peaks of $\lambda_{max}$=1550 nm ($\epsilon$=9330 $M^{-1}cm^{-1}$) and 1603 nm ($\epsilon$=11750 $M^{-1}cm^{-1}$), respectively. When in the $Ru^{2+}/Ru^{2+}$ and $Ru^{3+}/Ru^{3+}$ states, the complexes do not absorb in the region of 1000 and 1800 nm. The three states of these symmetric complexes can be switched from one to another by applying different potentials and bias.

Two major problems associated with these symmetric complexes (I) are (1) that the potential gap between the NIR-active state ($Ru^{2+}/Ru^{3+}$) and NIR-inactive state ($Ru^{2+}/$ $Ru^{2+}$ and $Ru^{3+}/Ru^{3+}$) is rather small, typically less than 0.57 V (or 570 mV), which makes the optical attenuation of a VOA very difficult to control electrically and (2) that these compounds do not form a thin film on an electrode (e.g., Indium-doped Tin Oxide or ITO), thus preventing the fabrication of an all-solid VOA device.

Thus, for VOA application, there is a need to have organic materials that have the chemical structures different from complexes I, but also are electroactive and are able to absorb and attenuate the light at the wavelengths of 1000 and 1800 nm.

Further, there is a need to have organic EC materials that have a large potential gap, ideally over 0.57 V or 570 mV between the NIR-active state and NIR-inactive state.

Further, there is a need to have organic EC materials that are able to form thin films on an electrode or to be deposited as thin films onto an electrode.

Finally, there is a need to have organic EC materials that can be crosslinked and form crosslinked polymeric films on electrodes for VOA device application.

BRIEF DESCRIPTION OF THE INVENTION

The present invention provides generally a new type of organic electrochromic NIR-active materials capable of absorbing and attenuating the light in the NIR region around 1550 nm and forming thin films on electrodes for VOA applications.

Five types of organic EC materials have been prepared, including unsymmetric ruthenium complex monomers containing two ruthenium metal ions per molecule, ruthenium complex dimers containing four ruthenium metal ions per molecule, ruthenium complex trimers containing six ruthenium metal ions per molecule, ruthenium complex polymers containing more than six ruthenium metal ions per polymer chain and crosslinked ruthenium complex films on electrodes.

DESCRIPTION OF THE DRAWINGS

The invention will be further described with respect to the drawings, in which.

DETAILED DESCRIPTION OF THE INVENTION

Ruthenium Complex Monomers

Figure 1:
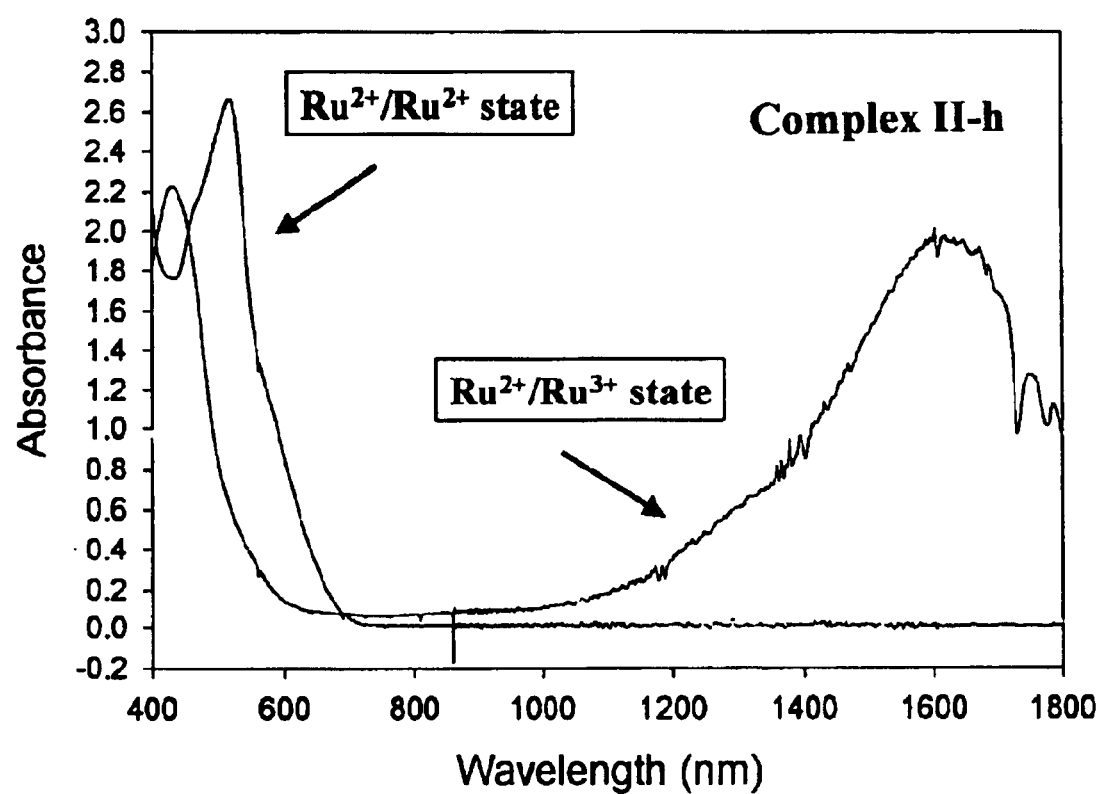
FIG. 1 is an in-situ spectroelectrochemical profile of complex II-h described below.

It has been found according to the invention that, in ruthenium complexes, the influence of the organic substituents can selectively perturb the metal ion associated with the ring bearing the particular substituent. Therefore, by pairing an electron donating substituent on one ring with that of an electron withdrawing substituent on the other ring, one ruthenium can be shifted cathodically while the other is shifted anodically. Therefore, the effect is to widen the potential gap between the individual metal Ru(II)→Ru(III) redox couples. This is important in order to produce practical devices in which it is possible to controllably select each of the oxidation states.

Therefore, one aspect of the present invention relates to a novel series of NIR electrochromic ruthenium complex monomers having a formula (II):

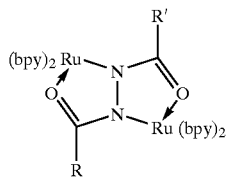

II where R and R' are different. Because the two groups are different, they will have different electron-withdrawing properties, so that one will tend to withdraw electrons and one will tend to donate electrons. Preferably, R and R' are selected from phenyl, nitrophenyl, methoxyphenyl, trifluoromethyl, N,N-dialkylamino, N-alkylamino, and alkyl groups. The alkyl groups most preferably are C1–C18 linear or branched chains. For the greatest potential gap, it is preferred to select two groups which have markedly different electron withdrawing properties. Thus, for example, if R is phenyl or alkyl (generally electron donating) then it is preferred for R' to contain nitrogen or fluorine (electron withdrawing).

Preparation of the ligands for complexes II is generally high yield and performed under mild conditions using reactive precursors. In these cases, the NMR spectra of the crude complex are generally devoid of peaks indicative of starting material and so recrystallization is not necessary. In the case of 1-benzoyl-2-trifluoroacetylhydrazine, evaporation of the solvent and excess of trifluoroacetic acid was sufficient to produce a product with acceptable purity.

Preparation of the complexes II gives generally high yield (e.g., 70% yield), using a known procedure used to make symmetrical complexes.[5], and using $Ru(bpy)_2Cl_2 \cdot 2H_2O$ prepared according to the method of Sullivan.[6] Isomeric complexes in three different oxidation states, namely $Ru^{2+}/Ru^{2+}$, $Ru^{2+}/Ru^{3+}$ and $Ru^{3+}/Ru^{3+}$ states, are produced during the reaction. If desired, these can be separated by any convenient known method, such as column chromatography on alumina, but it is not necessary to separate them for use as a VOA. In most cases, it is possible to isolate both the $Ru^{2+}/Ru^{2+}$ and $Ru^{2+}/Ru^{3+}$ isomeric complexes. However the $Ru^{3+}/Ru^{3+}$ isomer is produced in a small quantity only, and it is difficult to isolate.

All the complexes II exhibit a high degree of thermal stability as shown in Table 1. Typical onset temperatures ($T_d$) for 5% weight loss under nitrogen atmosphere) are high, in the range of 257–400° C. This stability is not surprising in light of the tight binding to be expected between ruthenium and three bidentate (i.e. two bipyridyl and 1,2-dicarbonylhydrazide) chelates which can engage in both c-donor and i-acceptor bonding interactions.

TABLE 1

Characterizations of ADC-Ru complexes II.

| Compound Number | ADC Ligand (R, R') | Yield (%) | $T_d^a$ (° C.) | $E_1^b$ (mV) | $E_2^b$ (mV) | ΔE ($E_2 - E_1$) |
|---|---|---|---|---|---|---|
| II-a | Ph, PhOCH$_3$ | 43 | 360 | 790 | 1360 | 570 |
| II-b | Ph, CF$_3$ | 58 | 377 | 970 | 1540 | 570 |
| II-c | Ph, CH$_3$ | 57 | 373 | 730 | 1330 | 600 |
| II-d | Ph, PhNO$_2$ | 44 | 350 | 880 | 1480 | 600 |
| II-e | Ph, N(CH$_3$)$_2$ | 43 | 311 | 650 | 1150 | 500 |
| II-f | Ph, NHPr-n | 41 | 257 | 590 | 1220 | 630 |
| II-g | PhOCH$_3$, CF$_3$ | | 400 | 960 | 1520 | 560 |
| II-h | PhOCH$_3$, CH$_3$ | | 400 | 740 | 1320 | 580 |
| II-i | PhOCH$_3$, PhNO$_2$ | | 360 | 850 | 1420 | 570 |
| II-j | PhOCH$_3$, N(CH$_3$)$_2$ | | 334 | 630 | 1080 | 450 |
| II-k | PhOCH$_3$, NHPr-n | | 311 | 560 | 1170 | 610 |
| II-l | PhNO$_2$, NHPr-n | | 313 | 660 | 1300 | 640 |

$^a$Onset temperature for 5% weight loss in nitrogen.
$^b$From cyclic voltammetry (CV) performed at 200 mV/s scan rate. The first potential $E_1$ for the $Ru^{2+}/Ru^{2+}$ state and the second potential $E_2$ for the $Ru^{2+}/Ru^{3+}$ state vs. NHE, taken in acetonitrile containing 0.1 M tetra-n-butylammonium hexafluorophosphate.
"Pr-n" stands for "n-propyl" and "Ph" stands for "phenyl" in this table and elsewhere in this document.

As the average donor strength of the substituent is increased, the E half potential shifts toward potentials that are more negative. At the same time the difference in the E half potentials (ΔE) between two redox couples generally drops. However, the most marked exceptions were the complexes II-f, II-k and II-l, which shows the largest differential over 600 mV All the unsymmetric ADC-Ru complexes II exhibit two reversible, positive one-electron redox couples associated with the ruthenium metal ions and, in some complexes only, two reversible, negative two-electron couples associated with the bipyridine ligands.

Pertaining to the dinuclear complexes II, the $Ru^{2+}/Ru^{2+}$ oxidation state of the complex exhibit two absorption bands associated with the $d(Ru^{2+}) \rightarrow \pi^*(bpy)$ metal to ligand charge transfer (MLCT) transitions in the visible region, which can be controlled by the applied redox potentials. Over the series there is slight decrease overall in the MLCT band energy (ca. 850 cm$^{-1}$) with increasing donor capacity of the substituents R and R' in II. Oxidation to the $Ru^{2+}/Ru^{3+}$ state results in the formation of an intense NIR band, associated with the metal to metal charge transfer (MMCT) transition, $d\pi(Ru^{2+}) \rightarrow d\pi(Ru^{3+})$, between 1000 to 1800 nm and typically within the telecommunication wavelengths of 1300–1600 nm (Table 2).

TABLE 2

Major absorption bands for complexes IIa-l in two oxidation states.

| Compound Number | R, R' | Total # of Ru charges | $\lambda_{max}(\log \epsilon)^a$ |
|---|---|---|---|
| II-a | Ph, CF$_3$ | 4 | 353 (4.28), 498 (4.21) |
| | | 5 | 1655 (4.04) |
| II-b | Ph, PhNO$_2$ | 4 | 293 (4.91), 352 (4.25), 513 (4.18) |
| | | 5 | 1612 (4.07) |
| II-c | Ph, PhOCH$_3$ | 4 | 294 (4.88), 354 (4.25), 519 (4.16) |
| | | 5 | 1590 (4.07) |
| II-d | Ph, CH$_3$ | 4 | 292 (4.93), 350 (4.24), 522 (4.18) |
| | | 5 | 1557 (4.08) |

TABLE 2-continued

Major absorption bands for complexes IIa-l in two oxidation states.

| Compound Number | R, R' | Total # of Ru charges | $\lambda_{max}$(log $\epsilon$)[a] |
|---|---|---|---|
| II-e | Ph, N(CH$_3$)$_2$ | 4 | 354 (4.23), 519 (4.13) |
|  |  | 5 | 1378 (3.77) |
| II-f | Ph, NHPr-n | 4 | 348 (4.20), 521 (4.12) |
|  |  | 5 | 1246 (3.71) |
| II-g | PhOCH$_3$, CF$_3$ | 4 | 354 (4.24), 499 (4.16) |
|  |  | 5 | 1639 (3.91) |
| II-h | PhOCH$_3$, PhNO$_2$ | 4 | 288 (4.93), 458 (4.06) |
|  |  | 5 | 1600 (3.54) |
| II-i | PhOCH$_3$, CH$_3$ | 4 | 348 (4.23), 523 (4.15) |
|  |  | 5 | 1556 (4.04) |
| II-j | PhOCH$_3$, N(CH$_3$)$_2$ | 4 | 288 (4.95), 351 (4.16) |
|  |  | 5 | 1354 (3.58) |
| II-k | PhOCH$_3$, NHPr-n | 4 | 289 (4.95), 346 (4.15), 455 (4.10) |
|  |  | 5 | 1253 (3.57) |
| II-l | PhNO$_2$, NHPr-n | 4 | 288 (4.97), 455 (4.13) |
|  |  | 5 | 1224 (3.05) |

[a]Measured in acetonitrile. Wavelengths in nm and molar extinction coefficients $\epsilon$ in M$^{-1}$ cm$^{-1}$ All the complexes II exhibit an ability of switching electrochemically between the NIR-inactive state and the NIR-active or NIR-absorbing state. FIG. 1 is an in-situ spectroelectrochemical profile of complex II-h. As a typical example shown in FIG. 1, complex II-h in solution displays two absorption peaks, one in the visible region (about 458 nm) for the Ru$^{2+}$/Ru$^{2+}$ state and another in the NIR region near 1550 nm for the Ru$^{2+}$/Ru$^{3+}$ state, which can be switched in-situ upon electrochemical oxidation and reduction.

Another series of dinuclear ruthenium complexes, structurally similar to complexes II, is set out in formula IV, wherein the two R groups can be different or the same within the same complex and are selective from hydrogen, alkyl, aryl, haloalkyl, hydroxyalkyl, —NH$_2$, or NR$_1$R$_2$ with R$_1$ and R$_2$ being alkyl or aryl. Optionally, R$_1$ and R$_2$ can be substituted with other functional groups. Preferred such other functional groups are carboxylic acid (—COOH), hydroxyl (—OH), amino (—NH$_2$), acetylenic, alkenylenic and thio (—SH).

The particularly preferred R groups are those shown in Scheme 1 below under IVa to IVe inclusive.

Scheme 1.
General synthesis of oxamide-Ru complexes IV.

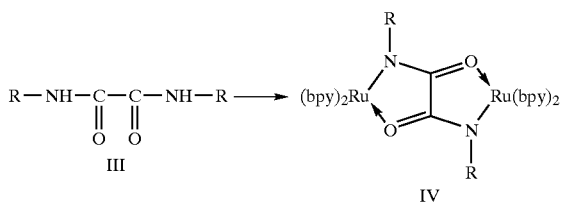

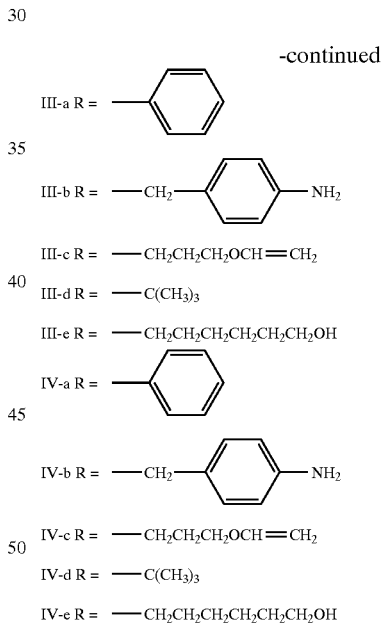

III-a R = —C$_6$H$_5$ (phenyl)

III-b R = —CH$_2$—C$_6$H$_4$—NH$_2$

III-c R = —CH$_2$CH$_2$CH$_2$OCH═CH$_2$

III-d R = —C(CH$_3$)$_3$

III-e R = —CH$_2$CH$_2$CH$_2$CH$_2$CH$_2$CH$_2$OH

IV-a R = —C$_6$H$_5$ (phenyl)

IV-b R = —CH$_2$—C$_6$H$_4$—NH$_2$

IV-c R = —CH$_2$CH$_2$CH$_2$OCH═CH$_2$

IV-d R = —C(CH$_3$)$_3$

IV-e R = —CH$_2$CH$_2$CH$_2$CH$_2$CH$_2$CH$_2$OH

Complexes IV are prepared using oxamide ligands III as shown in Scheme 1. The oxamide ligands having a generic structure of III are able to form the Ru complexes IV, which also are electroactive and electrochromic in the NIR region. The complexes are formed using any suitable method. The methods used in the prior art to form symmetric oxamide compounds, such as those shown in U.S. Pat. No. 4,978,786 of Messina et al., can be used to form the oxamide ligands.

The potential gap for IV is found to be in the range of 420 mV and 490 mV. The typical electrochemical data are listed below.

IV-a: $E_{1/2}$ potentials (100 mV/s, vs. NHE): 588 mV and 1008 mV ($\Delta$E=420 mV).

IV-b: $E_{1/2}$ potentials (100 mV/s, vs. NHE): 400 mV and 838 mV ($\Delta E$=438 mV).

IV-c: $E_{1/2}$ potentials (100 mV/s, vs. NHE): 607 mV and 1039 mV ($\Delta E$=432 mV).

IV-d: $E_{1/2}$ potentials (100 mV/s, vs. NHE): 636 mV and 1092 mV ($\Delta E$=456 mV).

IV-e: $E_{1/2}$ potentials (100 mV/s, vs. NHE): 605 mV and 1095 mV ($\Delta E$=490 mV).

The complexes IV show the NIR electrochromic properties similar to complexes II, suitable for use in optical variable attenuators. For example, IV-e displays a strong absorption band centered at 1658 nm when being in the $Ru^{2+}/Ru^{3+}$ state and has absorption bands in the visible region (e.g., 379, 528 and 630 nm) when being in either $Ru^{2+}/Ru^{2+}$ or $Ru^{3+}/Ru^{3+}$ oxidation state. Some of them bearing reactive groups such as IV-b, IV-c and IV-e could be crosslinked either chemically or photochemically to form a thin film on electrodes.

Ruthenium Complex Dimers

The present invention also relates to a novel series of ruthenium complex dimers of a formula VI, which are also capable of absorbing and attenuating the light in the NIR region and forming thin films on electrodes for VOA device fabrication. The R and R' groups in VI can be different or same within the same complex molecule and are hydrogen, alkyl, aryl, haloalkyl, hydroxyalkyl, —$NH_2$, $NR_1R_2$ with $R'_1$ and $R_2$ being alkyl or aryl. Optionally, $R'_1$ and $R_2$ can be substituted with other functional groups. Preferred such other functional groups are carboxylic acid (—COOH), hydroxyl (—OH), amino (—$NH_2$), acetylenic, alkenylenic and thio (—SH).

Most preferably, R in VI is phenyl and R' are those shown in Scheme 2.

Complex dimers VI are prepared under similar conditions as those for the preparation of ruthenium complex monomers II and IV, but using the corresponding ligands V. The complex dimers generally showed the same thermal stability as II and IV, except the ethylene and acetylene bridged systems (VI-c and VI-d) that had relatively lower decomposition temperatures.

Complex dimers VI show between two and four distinct redox couples (Table 3) and quite large potential gaps (560, 570 and 590 mV) between the NIR-inactive state and NIR-absorbing state. For the phenylene (VI-a) and butylene (VI-b) bridged complexes, two-electron couples were observed by cyclic voltammetry (CV). These can be assigned to the $1^{st}$ and $2^{nd}$ one-electron Ru(II)⇌Ru(III) couples of each of the linked dinuclear ADC complexes. It is relatively simple to rationalize the result for VI-b, as this is a saturated bridge and lacks any degree of conjugation.

In the case of the ethenylene (VI-c) and acetylene (VI-d) bridged complexes, between three and four redox couples are observed. Speaking on a case-by-case basis, VI-c showed four redox couples that appeared as two closely spaced pairs at approximately the same position as that of the other ruthenium complex dimers. Each couple appeared to possess the same current magnitude and can be assigned as four one-electron couples.

Scheme 2.
General synthesis of ruthenium complex dimers of a formula VI.

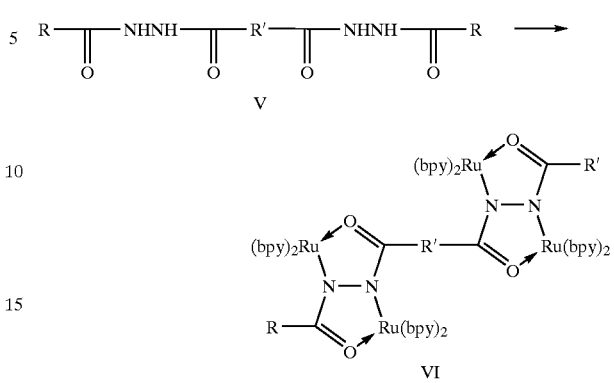

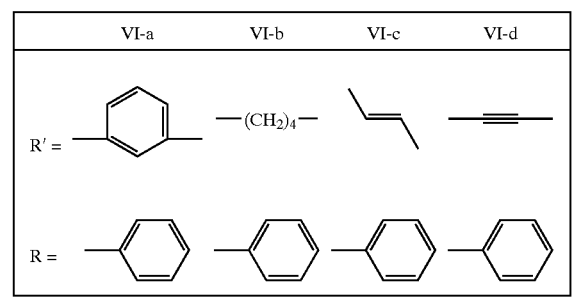

The acetylene bridged complex VI-d only shows three redox couples which, by the current density, are assigned as two one-electron couples ($1^{st}$ and $2^{nd}$ couple) and one two-electron couple ($3^{rd}$ couple). The $1^{st}$ redox couple is assigned to the Ru(II)Ru(II)⇌Ru(II)Ru(III) couple of one ADC fragment, the second assigned to the Ru(II)Ru(II)⇌Ru(II)Ru(III) of the other fragment, while the third to the two one-electron redox couples of both fragments.

TABLE 3

Electrochemical data[a] for ruthenium complex dimers VI-a-d.

| | $E^1$ | $E^2$ | $E^3$ | $E^4$ | $\Delta E$ |
|---|---|---|---|---|---|
| VI-a | 850 | 1440 | — | — | 590 ($E^2 - E^1$) |
| VI-b | 770 | 1340 | — | — | 570 ($E^2 - E^1$) |
| VI-c | 890 | 980 | 1540 | 1570 | 90 ($E^2 - E^1$) |
| | | | | | 560 ($E^3 - E^2$) |
| | | | | | 30 ($E^4 - E^3$) |
| VI-d | 780 | 1370 | 1550 | — | 590 ($E^2 - E^1$) |
| | | | | | 180 ($E^3 - E^2$) |

[a]From cyclic voltammetry performed in acetonitrile containing 0.1 M tetra-n-butylammonium hexafluorophosphate at 200 mV/s scan rate. Potentials E in mV vs. NHE.

Pertaining to the ruthenium complex dimers VI, there are several oxidation states that can be achieved by changing the applied potentials. There is always one state, in which the complex absorbs strongly between 1100 to 1800 nm and centered near 1550 nm (Table 4).

TABLE 4

Major absorption bands for complexes VI in three oxidation states.

| | Total # of Ru charges | $\lambda_{max}(\log \epsilon)^a$ |
|---|---|---|
| VI-a | 4 | 294 (5.15), 357 (4.52), 518 (4.44) |
| | 6 | 290 (5.11), 431 (4.31), 1575 (4.31) |
| | 8 | 306 (4.90), 316 (4.90), 798 (4.30) |
| VI-b | 4 | 245 (4.92), 293 (5.20), 348 (4.49), 520 (4.43) |
| | 6 | 242 (4.93), 291 (5.11), 434 (4.46), 1510 (4.38) |
| | 8 | 248 (5.00), 304 (4.87), 316 (4.86), 802 (4.48) |
| VI-c | 4 | 245 (4.92), 288 (5.20), 358 (4.49), 464 (4.48), 508 (4.46) |
| | 6 | 244 (4.91), 288 (5.16), 449 (4.46), 1645 (4.22) |
| | 8 | 246 (4.97), 303 (4.92), 801 (4.12) |
| VI-d | 4 | 244 (4.46), 287 (4.86), 452 (3.99) |
| | 5 | 243 (4.47), 287 (4.81), 449 (4.06), 1579 (3.63) |
| | 6 | 248 (4.56), 304 (4.55), 809 (3.55) |
| | 8 | 247 (4.59), 305 (4.58), 797 (3.53) |

$^a$Measured in acetonitrile. Wavelengths in nm and molar extinction coefficients $\epsilon$ in $M^{-1}$ $cm^{-1}$

Ruthenium Complex Trimers

The present invention also relates to a series of ruthenium complex trimers of a formula VIII, which are prepared from the corresponding ADC-type ligands VII as shown in Scheme 3. The R groups in VIII can be different or same within the same complex molecule and are hydrogen, alkyl, aryl, haloalkyl, hydroxyalkyl, —NH$_2$, NR$_1$R$_2$ with R'$_1$ and R$_2$ being alkyl or aryl. Optionally, R'$_1$ and R$_2$ can be substituted with other functional groups. Preferred such other functional groups are carboxylic acid (—COOH), hydroxyl (—OH), amino (—NH$_2$), acetylenic, alkenyleric and thio (—SH).

The most preferred R groups in VIII are those shown in Scheme 3. The complexes VIII also show the desired electrochromic property similar to complexes II, IV and VI in the NIR region and some of them could be crosslinked to form thin films on electrodes.

Scheme 3.
General synthesis of ruthenium complex trimers of formula VIII.

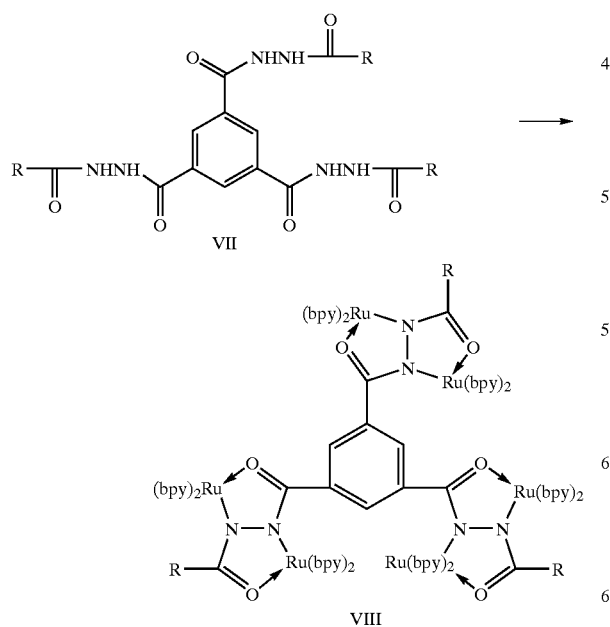

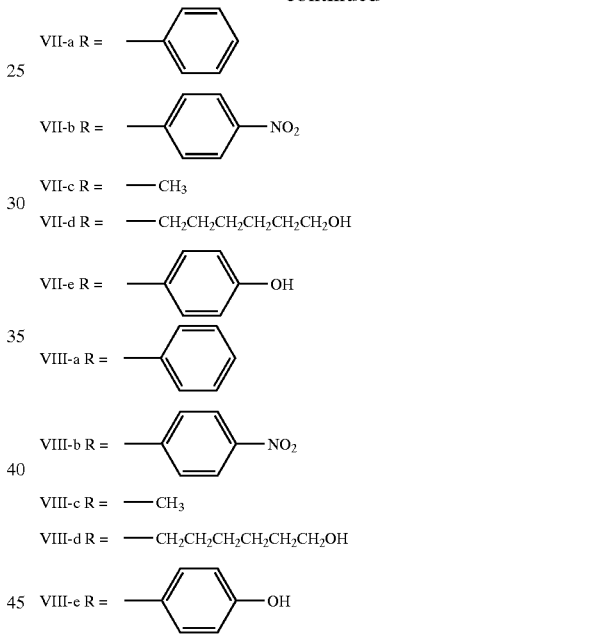

VII-a R = —(phenyl)

VII-b R = —(phenyl)—NO$_2$

VII-c R = —CH$_3$

VII-d R = —CH$_2$CH$_2$CH$_2$CH$_2$CH$_2$CH$_2$OH

VII-e R = —(phenyl)—OH

VIII-a R = —(phenyl)

VIII-b R = —(phenyl)—NO$_2$

VIII-c R = —CH$_3$

VIII-d R = —CH$_2$CH$_2$CH$_2$CH$_2$CH$_2$CH$_2$OH

VIII-e R = —(phenyl)—OH

Ruthenium Complex Polymers

The present invention also relates to a new series of ruthenium complex polymers XI and XII that are derived from the polymeric ligands of formulae IX and X, respectively and are also capable of absorbing and attenuating the light in the NIR region and forming thin films on electrodes.

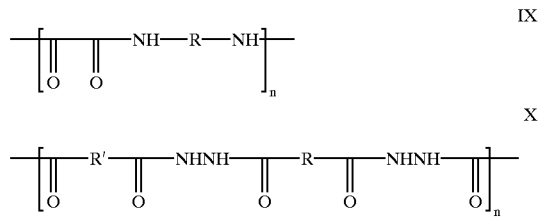

The R group in IX can be nil (i.e. no —R— group at all), alkylene and arylene, with either of the arylene or alylene connecting group containing other functional groups. The other functional groups are preferably halo, acetylenic, alkenylenic, nitro or cyano. Further, the R group in IX can be oligomeric units of polyolefins, polyethers, poly(ethylene glycol)s, polycarbonate, polyesters, polyurethanes, polyamides, polyimides and any other copolymers. Preferably, the R group in IX is any of C2–C18 alkylenes and oligomeric units of poly(alkylene oxide)s. The most preferred R groups are those shown in polymers IX-a and IX-b wherein m is from 1 to 100 and preferably 10–12.

IX-a: R = —CH$_2$—CH(CH$_3$)—CH$_2$—CH$_2$—CH$_2$—

IX-b: R =

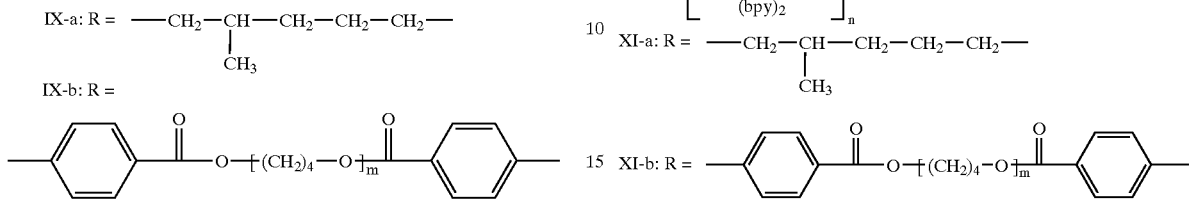

The polymeric ligands IX can be synthesized by solution polymerization in toluene, xylenes, 1,2-dichloroethane, 1,1,2,2-tetrachloroethane, o-dichlorobenzene, methylene chloride, chloroform, N,N-dimethylformamide (DMF). N,N,-dimethylacetamide (DMAc), N-methylpyrrolidinone (NNW), and other chlorinated or non-halogenated hydrocarbon and aromatic solvents. The said polymerization is preferred to be carried out in DMF when diethyl oxalate being used or toluene when oxalyl chloride being used.

The R and R' groups in X can be different or same within the same polymer and can be alkylene and arylene, any of the later two connectors containing other functional groups such as halo, acetylenic, alkenylenic, nitro and cyano. Further, the R group in IX can be oligomeric units of polyolefins, polyethers, poly(ethylene glycol)s, polycarbonate, polyesters, polyurethanes, polyamides, polyimides and any other copolymers. Preferably, the R and R' group in X are any of C2–C18 alkylenes, diaminoalkylenes containing C2–C18 chains and ortho-, meta- or para-phenylenes. The most preferred R and R' are those shown in polymers X-a: R=n-butylene R'=m-phylene
X-b: R=n-butylene R'=n-butylene
X-c: R=m-phylene R'=m-phylene
X-d: R=n-butylene R'=—NH(CH$_2$)$_6$NH—
X-a, X-b, X-c and IX-d.

The present invention also provides two general methods for incorporation of the ruthenium metals into the above polymeric ligands IX and X. The first method involves the use of Ru(bpy)$_2$Cl$_2$ as an exchanging agent at the temperatures ranging from 0° C. to the boiling point of a given solvent including, but not limiting, methanol, ethanol, water, any of C3–C10 linear or branched alcohols, DMF, DMAc, and NMP or a combination of any of these said solvents in any ratio and in the presence of an inorganic base including but not limiting sodium hydroxide, potassium hydroxide, sodium bicarbonate, potassium bicarbonate, sodium carbonate, potassium carbonate and any of tertiary aliphatic amines such as triethylamine. The second method for incorporating the ruthenium metal into polymeric ligands involves the use of Ru(bpy)$_2$(acetone)$_2$(OTf)$_2$, as an exchanging agent, under the same conditions as the first method. The said exchanging agent is derived in any way known to the art. A particularly convenient way is from Ru(bpy)$_2$Cl$_2$·2H$_2$O upon treatment with silver trifluoromethanesulfonate in acetone. Wnem ontained this way, the exchanging agent can be used in the subsequent reaction without further purification and storage.

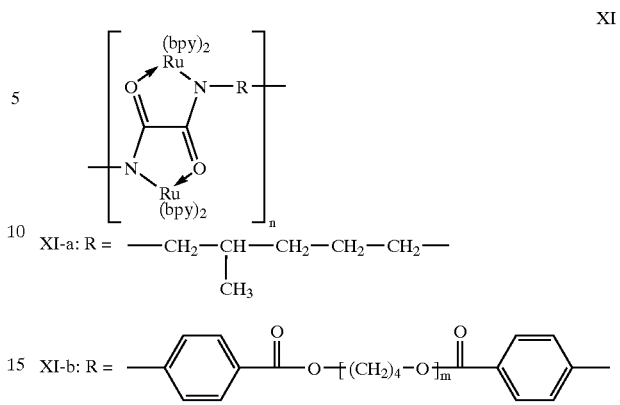

XI-a: R = —CH$_2$—CH(CH$_3$)—CH$_2$—CH$_2$—CH$_2$—

XI-b: R =

XII-a: R=n-butylene R'=m-phylene
IIX-b: R=n-butylene R'=n-butlene
XII-c: R=m-phylene R'=m-phylene
XII-d: R=n-butylene R'=—NH(CH$_2$)$_6$NH—

Both methods can be used with any of polymeric ligands to prepare ruthenium complex polymers. Preferrably, ruthenium complex polymers XI are prepared by the said second method from polymeric ligands IX and ruthenium complex polymers XII are prepared by the said first method from polymeric ligands X. The ruthenium content present in polymers XI and XII can be controlled by varying the reaction conditions such as the amount of an exchanging agent used, reaction temperatures and reaction time for the first or second method and is in the range of 1% to 85% by weight. Typically, the ruthenium content in XI and XII is between 10% to 50% by weight.

All the ruthenium complex polymers XI and XII are soluble in common organic solvents such as acetone, acetonitrile, chloroform and DMF and can be cast or spin coated into a thin film directly on an electrode such as ITO electrode, making them well suited for VOA applications.

Crosslinked NIR Electrochromic Polymer Films on Electrodes

The present invention also relates to crosslinked ruthenium complex polymer films on electrodes for VOC device applications, using ruthenium complex monomers IV and trimers VIM together with any of diisocyanate or triisocyanate oligomers and polymers. Preferably, ruthenium complex monomers (IV-b and IV-e) and trimers (VIII-d and VIII-e) are used together with a triisocyanate or diisocyanate, to form crosslinked polymer films on electrodes. Preferably, the triisocyanates are those that are prepared from trimethylol propane and the diisocyanates are toluene diisocyanate, xylylene diisocyanate, hexahydroxylylene diisocyanate and hexamethylene diisocyanate. In a preferred embodiment, the ruthenium complex trimer VIII-e is used together with a triisocyanate derived from trimethylol propane and xylylene diisocyanate, with molar ratios of ruthenium trimer/triisocyanate being in the range of 1.0/1.0 to 1.0/2.0, to form a thin film directly on ITO electrode. The crosslinking or cure can be effected at elevated temperatures in the range of 25–200° C., preferably in the range of 80–150° C. and specifically at 110° C., after applying the prepolymer solution of VIII-e and the said triisocyanate in a common organic solvent including but not limiting acetonitrile, aromatic hydrocarbons, chlorinated solvents, DMF, DMAc and NMP, preferably in acetonitrile with a concentration ranging from 5% to 25% by weight per mL, onto ITO electrode using a common method such as casting, spin coating, dip coating or spray coating. The cured film on ITO electrode is not be re-dissolved or peeled off in a variety of organic solvents and water, such as acetone, acetonitrile, methanol, ethanol and DMF. The cured films on ITO exhibit the same electrochemical behavior as the ruthenium complex monomers II and IV, dimers VI, trimers VIII and polymers XI and XII in solution, making these films well suited for VOA applications.

Figure 2:
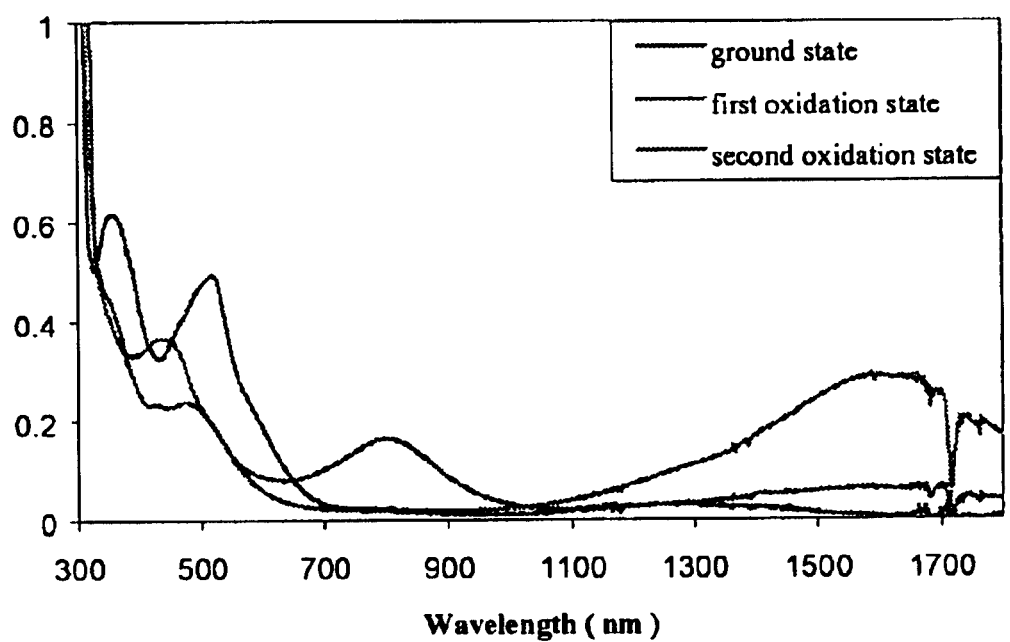
FIG. 2 shows spectroelectrochemical spectra of a Ru complex film in acetonitrile.
Figure 3:
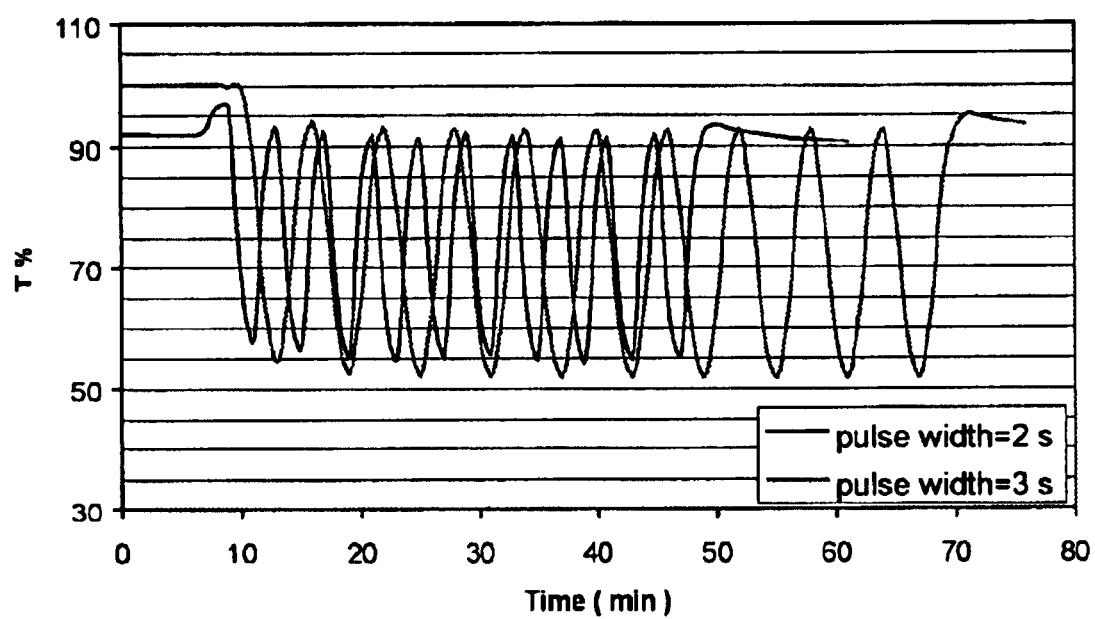
FIG. 3 shows transmission spectra of ruthenium complex film at 1550 nm with different pulse widths.

The NIR electrochromism of the crosslinked film on ITO electrode is shown in FIG. 2. The NIR absorption around 1550 nm appears repeatedly when the ruthenium complex film is electrically switched to the first oxidation state where the two Ru metals in the repeat unit exist as the $Ru^{2+}/Ru^{3+}$ state, from either the ground state or the second oxidation state. Optical attenuation at 1550 nm of the complex film having a thickness of 408 nm on ITO, which is placed in acetonitrile containing tetra-n-butylammonium hexafluorophosphate as electrolyte, reaches 2.8 dB when pulse width is set at 3 seconds and reached 2.2 dB with 2 seconds of pulse width (FIG. 3). Accordingly, optical attenuation at 1550 nm for this ruthenium complex film is 6.9 dB per micron of film thickness. The film stability in solution was tested over 18000 cycles, which showed that after 7500 switching cycles the attenuation range dropped by 9% and after 18750 cycles the attenuation range dropped about 15% of the original value.

The following examples are illustrative of the present invention y and do not limit the scope of the invention or the claims.

Example 1

Preparation of Symmetric ADC Ligands for Ruthenium Complex Monomers II

All the ADC ligands for making complexes II were synthesized from the appropriate hydrazide and either the appropriate acid chloride, acid anhydride or isocyanate. The specific synthetic environment was varied to permit reasonable yields, however generally they were produced in THF with a stoichiometric amount of triethylamine (TEA) added to remove the by-product HCl.

1-Acetyl-2-benzoylhydrazine: 1.5 g (11.2 mmol) of benzoylhydrazide was dissolved in 40 mL of THF. While agitating, to this solution was added 1.11 g (11.0 mmol) of TEA followed by the slow addition of 0.86 g (11.0 mmol) of acetyl chloride. TEA.HCl formed almost immediately and was removed by filtration. The filtrate was then rotary evaporated to remove the solvent and dried in vacuo overnight yielding 1.1 g (55% yield) of crude product. Recrystallization from $EtOH/H_2O$ afforded a white, crystalline product. $^1H$ NMR (200 MHz, $d_6$-DMSO) δ 1.94 (s, 3H), 7.54 (m, 3H), 7.88 (d, 2H), 9.91 (s, 1H), 10.31 (s, 1H); MS (EI, m/e) calcd for $C_9H_{10}N_2O_2$ 178, found 178 ($M^+$, 6.1); mp 172–174° C.

1-Benzoyl-2-trifluoroacetylhydrazine: 1.5 g (11.2 mmol) of benzoylhydrazide and 2.0 g (9.3 mmol) of $(CF_3CO)_2O$ were added to 20 mL of THF. After the solution cooled to room temperature, the crude product was obtained after removal of solvent by rotary evaporation. Yield was 1.9 g (73%). $^1H$ NMR (200 MHz, $d_6$-DMSO) δ 9.55 (m, 3H), 9.90 (d, 2H), 10.81 (s, 1H), 11.65 (s, 1H); MS (EI, m/e, relative intensity %) calcd for $C_9H_7N_2O_2F_3$ 232, found 232 ($M^+$, 12.9); mp 153–154° C.

1-Benzoyl-2-(N,N-dimethylcarbamyl)hydrazine: Synthesis and isolation were same as 1-acetyl-2-benzoylhydrazine, using 1.5 g (11.2 mmol) of benzoylhydrazide, 1.2 g (11.2 mmol) of $(CH_3)_2NCOCl$ and 1.11 g of TEA. Yield was 0.9 g (39%). $^1H$ NMR (200 MHz, $d_6$-DMSO) δ 2.90 (s, 6H), 7.50 (m, 3H), 7.90 (d, 3H), 8.45 (s, 1H), 10.05 (s, 1H); MS (EI, m/e, relative intensity %) calcd for $C_{10}H_{13}N_3O_2$ 207, found 207 (M, 13.2); mp 199–201° C.

1-Benzoyl-2-(N-propylcarbamyl)hydrazine: 1.5 g (11.2 mmol) of benzoylhydrazide and 1.0 g (11.7 mmol) of n-propylisocyanate were combined in 20 mL of TBF. The product precipitated from solution almost immediately and after waiting approx. 30 minutes to ensure that the reaction had reached completion, the product was isolated by filtration The residue was washed with TIE and diethyl ether. Yield was 1.87 g (75%). $^1H$ NMR (200 MHz, $d_6$-DMSO) δ 0.85 (t, 3H), 1.40 (m, 2H), 3.05 (m, 2H), 6.50 (s, 11), 7.55 (m, 3H), 7.85 (s, 1H), 7.95 (d, 2H), 10.10 (s, 1H); MS (EI, m/e, relative intensity %) calcd for $C_{11}H_{15}N_3O_2$ 221, found 221 ($M^+$, 2.7); mp 172–174° C.

1-Benzoyl-2-(4-nitrobenzoyl)hydrazine: 1.5 g (11.2 mmol) of benzoylhydrazide was dissolved in 20 mL of water and 2.0 g (10.8 mmol) of $O_2NPhCOCl$ was dissolved in 20 mL of toluene. The two solutions were then combined and vigorously agitated for 10 hours. The product precipitated and was isolated by filtration to yield 2.6 g (81%) of the crude product. $^1H$ NMR (200 MHz, $d_6$-DMSO) δ 7.57 (m, 31), 7.93 (m, 21), 8.16 (d, 2H), 8.38 (d, 2H), 10.69 (s, 1H), 10.91 (s, 1H); MS (EI, m/e, relative intensity %) calcd for C14 $H_{11}N_3O_4$ 285, found 285 (M, 4.7); mp 254–256° C.

1-Benzoyl-2-(4-methoxybenzoyl)hydrazine: Synthesis and isolation were same as 1-acetyl-2-benzoylhydrazine, using 1.5 g (11.2 mmol) of benzoylhydrazide, 1.9 g (11.1 mmol) of 4-methoxybenzoylchloride and 1.1 g of TEA. Yield was 2.9 g (97%). $^1H$ NMR (200 MHz, $d_6$-DMSO) δ 5.13 (s, 3H), 8.36 (d, 2H), 8.86 (m, 3H), 9.23 (d, 4H) 11.72 (d, 2H); MS (EI, m/e, relative intensity %) calcd for $C_{15}H_{14}N_2O_3$ 270, found 270 ($M^+$, 5.1); mp 201–202° C.

1-(4-Methoxybenzoyl)-2-(4-nitrobenzoyl)hydrazine: 1.8 g (10.8 mmol) of 4-methoxybenzoylhydrazine was suspended in 25 mL of water and combined with 2.0 g (10.8 mmol) of $O_2NPhCOCl$ dissolved in 25 mL of toluene. The mixture was then set to reflux for 2 hours, cooled to room temperature followed by precipitation of the product in methanol. Yield was 3.2 g (94%). MS (EI, m/e) calcd for $C_{15}H_{13}N_3O_5$ 315, found 315 ($M^+$, 2.3); mp 256–258° C.

1-(4-Methoxybenzoyl)-2-trifluoroacetylhydrazine: Synthesis and isolation were same as I-benzoyl-2-trifluoroacetylhydrazine, using 1.8 g (10.8 mmol) of 4-methoxybenzoylhydrazine and 2.0 g (9.5 mmol) of $(CF_3CO)_2O$. Yield was 2.4 g (85%). MS (EI, m/e) calcd for $C_{10}H_9F_3N_2O_3$ 262, found 262 ($M^+$, 8.0); mp 147–148° C.

1-Acetyl-2-(4-methoxybenzoyl)hydrazine: To 40 mL of THF were added 1.8 g (10.8 mmol) of 4-methoxybenzoylhydrazine, 0.9 g (11.5 mmol) of acetyl chloride and 1.1 g of TEA. The reaction mixture was stirred for 1 hour, followed by evaporation off ca. ½ volume of THF. The product was precipitated into methanol, filtered and dried over night under vacuum. Yield was 2.14 g (95%).

MS (EI, m/e) calcd for $C_{10}H_{12}N_2O_3$ 208, found 208 M$^+$, 6.7); mp 146–148° C.

1-(N,N-Dimethylcarbamyl)-2-(4-methoxybenzoyl) hydrazine: Synthesis and isolation were same as for 1-acetyl-2-benzoylhydrazine, using 1.8 g (10.8 mmol) of 4-methoxybenzoylhydrazine, 1.2 g (11.1 mmol) of $(CH_3)_2NCOCl$, and 1.1 g of TEA. Yield was 1.5 g (59%). MS (EI, m/e) calcd for $C_{11}H_{15}N_3O_3$ 237, found 237 (M$^+$, 8.3); mp 218–220° C.

1-(4-Methoxybenzoyl)-2-(N-propylcarbamyl)hydrazine: Synthesis and isolation were same as for 1-benzoyl-2-(N-propylcarbamyl)hydrazine, using 1.3 g (7.8 mmol) 4-methoxybenzoylhydrazine and 0.9 g (10.5 mmol) of n-propylisocyanate. Yield was 1.8 g (92%). MS (EI, m/e) calcd for $C_{12}H_{17}N_3O_3$ 251, found 251 (M$^+$, 1.6); mp 176–179° C.

Example 2

Preparation of Ruthenium Complex Monomers II

All ruthenium complexes II were synthesized according to the known procedure,[5] using $Ru(bpy)_2Cl_2.2H_2O$ as an exchanging agent. The general synthetic procedure was to combine 0.38 mmol (200 mg) of $Ru(bpy)_2Cl_20.2H_2O$ with 0.19 mmol of the ADC ligand and 40 mg of NaOH or 106 mg of $Na_2CO_3$ in 80 mL of 5:1$H_2O$/EtOH. The mixture was then set to reflux for cp. 14 hours under ambient atmosphere, after which it was cooled to room temperatures, and the product was precipitated by the addition of excess $NH_4PF_6$. The crude product was then isolated by filtration, dried in vacuum (e.g., 5 mmHg), then purified via column chromatography on acid-type alumina gel using acetonitrile as the mobile phase.

II-a [{$Ru(bpy)_2$}$_2$ $\mu$-Ph,CF$_3$-adc](PF$_6$)$_2$: Using 200 mg (0.38 mmol) of $Ru(bpy)_2Cl_20.2H_2O$, 44 mg (0.19 mmol) of 1-benzoyl-2-trifluoroacetylhydrazine, and 106 mg of $Na_2CO_3$, yield of the purified product was 58%. FAB-MS (m/z, relative intensity %) calcd for $C_{49}F_3H_{37}N_{10}O_2Ru_2$ 1057, found 1057 (M$^+$, 0.7).

II-b [{$Ru(bpy)_2$}$_2\mu$-Ph,NO$_2$Ph-adc](PF$_6$)$_2$: Using 200 mg (0.38 mmol) of $Ru(bpy)_2Cl_20.2H_2O$, 54 mg (0.19 mmol) of 1-benzoyl-2-(4-nitrobenzoyl)hydrazine, and 40 mg of NaOH yield of the purified product was 44%. (FAB-MS (m/z, relative intensity %) calcd for $C54F_6H_{41}N_{11}O4PRu_2$ 1255, found 1255 (M$^+$, 9.8).

II-c [{$Ru(bpy)_2$}$_2$ $\mu$-Ph,CH$_3$OPh-adc](PF$_6$)$_2$: Using 200 mg (0.38 mmol) $Ru(bpy)_2Cl_20.2H_2O$, 48 mg (0.19 mmol) of 1-benzoyl-2-(4-methoxybenzoyl)hydrazine and 40 mg of NaOH, yield of the purified product was 43%; FAB-MS (m/z, relative intensity %) calcd for $C_{55}F_6H_{44}N_{10}O_3PRu_2$ 1240, found 1240 (W, 1.4).

II-d [{$Ru(bpy)_2$}$_2$ $\mu$-Ph, CH$_3$-adc](PF$_6$)$_2$: Using 200 mg (0.38 mmol) of $Ru(bpy)_2Cl_20.2H_2O$, 34 mg (0.19 mmol) of 1-benzoyl-2-acetylhydrazine, and 40 mg of NaOH, yield of the purified product was 57%. FAB-MS (m/z, relative intensity %) calcd for $C_{49}F_6H_{40}N_{10}O_2PRu_2$ 1148, found 1148 (M$^+$, 4.3).

II-e [{$Ru(bpy)_2$}$_2$ $\mu$-Ph,N(CH$_3$)$_2$-adc](PF$_6$)$_2$: Using 200 mg (0.38 mmol) of $Ru(bpy)_2Cl_20.2H_2O$, 39 mg (0.19 mmol) of 1-benzoyl-2-(N,N-dimethylcarbamyl) hydrazine, and 40 mg of NaOH, yield of the purified product was 43%. FAB-MS (m/z, relative intensity %) calcd for $C_{50}F_6H_{43}N_{11}O_2PRu_2$ 1177, found 1177 (M$^+$, 1.1).

II-f [{$Ru(bpy)_2$}$_2$ $\mu$-Ph,NH(CH$_2$CH$_2$CH$_3$)-adc](PF$_6$)$_2$: Using 200 mg (0.38 mmol) of $Ru(bpy)_2Cl_20.2H_2O$, 42 mg (0.19 mmol) of 1-benzoyl-2-(N-propylcarbamyl) hydrazine, and 40 mg of NaOH, yield of the purified product was 41%. FAB-MS (m/z, relative intensity %) calcd for $C_{51}F_6H_{44}N_{11}O_2PRu_2$ 1190, found 1190 (M$^+$, 6.4).

II-g [{$Ru(bpy)_2$}$_2$ $\mu$-CH$_3$OPh,CF$_3$-adc](PF$_6$)$_2$: Uusing 200 mg (0.38 mmol) of $Ru(bpy)_2Cl_20.2H_2O$, 50 mg (0.19 mmol) of 1-(4-methoxybenzoyl)-2-trifluoroacetylhydrazine, and 106 mg of $Na_2CO_3$, yield of the purified product was 50%. FAB-MS (m/z, relative intensity %) calcd for $C_{50}F_9H_{41}N_{10}O_3PRu_2$ 1233, found 1233 (M$^+$, 5.6).

II-h [{$Ru(bpy)_2$}$_2$ $\mu$-CH$_3$OPh, NO$_2$Ph-adc](PF$_6$)$_2$: Using 200 mg (0.38 mmol) of $Ru(bpy)_2Cl_20.2H_2O$, 60 mg (0.19 mmol) of 1-(4-methoxybenzoyl)-2-(4-nitrobenzoyl)hydrazine, and 40 mg of NaOH, yield of the purified product was 30%. FAB-MS (m/z, relative intensity %) calcd for $C_{55}F_6H_{45}N_{11}O_5PRu_2$ 1286, found 1286 (or, 19.7).

II-i [{$Ru(bpy)_2$}$_2$ $\mu$-CH$_3$OPh,CH$_3$-adc](PF$_6$)$_2$: Using 200 mg (0.38 mmol) of $Ru(bpy)_2Cl_20.2H_2O$, 40 mg of 1-(4-methoxybenzoyl)-2-acetylhydrazine, and 106 mg of $Na_2CO_3$, yield of the purified product was 70%. FAB-MS (m/z, relative intensity %) calcd for $C50F_6H_{44}N_{10}O_3PRu_2$ 1179, found 1179 (M$^+$, 5.1).

II-j [{$Ru(bpy)_2$}$_2$ $\mu$-CH$_3$OPh,N(CH$_3$)$_2$-adc](PF$_6$)$_2$: Using 200 mg (0.38 mmol) $Ru(bpy)_2Cl_20.2H_2O$, 45 mg (0.19 mmol) of 1-(N,N-dimethylcarbamyl)-2-(4-methoxybenzoyl)hydrazine, and 40 mg of NaOH, yield of the purified product was 32%. FAB-MS (m/z, relative intensity %) calcd for $C_{51}F_6H_{47}N_{11}O_3PRu_2$ 1208, found 1208 (M$^+$, 12.3).

II-k [{$Ru(bpy)_2$}$_2$ $\mu$-CH$_3$OPh,NH(C$_3$H$_7$)-adc](PF$_6$)$_2$: Using 200 mg (0.38 mmol) of $Ru(bpy)_2Cl_20.2H_2O$, 48 mg (0.19 mmol) of 1-(4-methoxybenzoyl)-2-(N-propylcarbamyl)hydrazine, and 40 mg of NaOH, yield of the purified product was 32%. FAB-MS (m/z, relative intensity %) calcd for $C_{52}F_6H_{49}N_{11}O_3PRu_2$ 1222, found 1222 (M$^+$, 6.9).

II-l [{$Ru(bpy)_2$}$_2\mu$-NO$_2$Ph,NH(C$_3$H$_7$)-adc](PF$_6$)$_2$: Using 200 mg (0.38 mmol) of $Ru(bpy)_2Cl_2$ 2H$_2$O, 51 mg of 1-(4-nitrobenzoyl)-2-(N-propylcarbamyl)hydrazine, and 40 mg of NaOH, yield of the purified product was 29%. FAB-MS (m/z, relative intensity %) calcd for $C_{51}F_6H_{46}N_{12}O_4PRu_2$ 1236, found 1236 (M$^+$, 24.8).

Example 3

Preparation of Ruthenium Complex Monomers IV

A typical procedure is given for the synthesis of IV-e as follows: A solution of HO(CH$_2$)$_6$NHCOCONH(CH$_2$)$_6$OH (0.056 g, 0.19 mmol), $Ru(bpy)_2Cl_20.2H_2O$ (0.20 g, 0.38 mmol), and sodium hydroxide (40 mg, 1.0 mmol) in a mixture of water/ethanol (5/1 v:v, 80 ml) was heated to reflux for 24 hours under argon. After cooling to room temperature, 1 gram ammonium hexafluorophosphate dissolved in 40 mL of water was added and dark-red precipitates formed. The precipitates were filtered off and re-dissolved in acetone (20 mL). The product IV-e was obtained by pouring the acetone solution into diethyl ether and was then dried under vacuum (5 mmHg) at room temperature. Yield was 35%; IR (KBr): 3425, 1583, 843 cm$^{-1}$; $E_{1/2}$ potentials (100 mV/s vs. NHE): 605 mV and 1095 mV.

Other ruthenium complex monomers are prepared in the same manner as described above and their electrochemical properties are shown below.

IV-a: $E_{1/2}$ potentials (100 mV/s, vs. NHE): 588 mV and 1008 mV (ΔE=420 mV).

IV-b: $E_{1/2}$ potentials (100 mV/s, vs. NHE): 400 mV and 838 mV (ΔE=438 mV).

IV-c: $E_{1/2}$ potentials (100 mV/s, vs. NE): 607 mV and 1039 mV (ΔE=432 mV).

IV-d: $E_{1/2}$ potentials (100 mV/s, vs. NHE): 636 mV and 1092 mV (ΔE=456 mV).

Example 4

Preparation of Ligands VII

VII-a: A solution of benzoic hydrazide (0.76 g, 5.6 mmol), 1,3,5-benzenetricarbonyl trichloride (0.50 g, 1.8 mmol), and pyridine (0.5 ml) in THF (10 mL) was stirred at 0° C. for 1 hour. Then the reaction mixture was allowed to warm to room temperature slowly and stirred for another 0.5 hour. The supernatant liquid was decanted and the solid product was washed with water and hot methanol to give a white powder (0.8 g, yield 85%). $^1$H NMR (200 MHz, DMSO-d$_6$): δ 10.9 (s, 3H); 10.7 (s, 3H); 8.7 (s, 3H); 7.9 (m, 6H); 7.5 (m, 9H) ppm; IR (KBr): 1657, 1602, 1264 cm$^{-1}$.

VII-b was prepared by the same procedure as VII-a. Yield was 72%. $^1$H NMR (200 MHz, DMSO-d$_6$): δ 11.0 (s, 3H); 8.7 (s, 3H); 8.4 (d, 6H); 8.2 (d, 6H) ppm,. IR (KBr): 3202, 1655, 1600, 1262 cm$^{-1}$.

VII-c was prepared by the same procedure as VII-a and recrystallized from water. Yield was 43%. $^1$H NMR (200 MHz, DMSO-d$_6$): δ 10.6 (s, 3H); 10.0 (s, 3H); 8.5 (s, 3H); 1.94 (s, 9H) ppm; IR (KBr): 3266, 1694, 1654, 1258 cm$^{-1}$.

VII-d: A solution of 1,3,5-benzenetricarbonyl trichloride (0.4 g, 1.5 mmol) in DMF (5 mL) was added dropwise into a solution of 6-hydroxy hexanoic hydrazide (0.74 g, 5 mmol) and triethylamine (0.7 mL) in DMF (10 mL). The solution was stirred at 0° C. for 1 hour, and then stirred at room temperature for another 1 hour. The reaction mixture was filtered to remove the hydrochloric salt of triethylamine. The filtrate was evaporated under reduced pressure, and the resultant viscous yellow liquid was boiled with a mixture of ethyl acetate/hexane (4:1 v/v) until the liquid turned white. The supernatant solution was decanted, and the residual liquid was dried under vacuum to give a pale white solid. Distilled water (10 mL) was used to wash the solid, and a white powdered product was obtained (0.2 g, yield 25%). $^1$H NMR (400 MHz, DMSO-d$_6$): (10.6 (s, 3H); 10.0 (s, 3H); 8.5 (s, 3H); 4.4 (t, 3H, J=5.2 Hz); 3.4 (dd, 6H, J=6.4 Hz, 5,2 Hz); 2.2 (t, 6H, J=7.2 Hz); 1.5 (m, 6H); 1.4 (m, 6H); 1.3 (m, 6H) ppm;. IR (KBr): 3200, 1697, 1654 cm$^{-1}$.

VII-e: A solution of 1,3,5-benzenetricarbonyl trichloride (0.56 g, 2.1 mmol) in DMF (5 mL) was added dropwise into a solution of p-hydroxybenzoic hydrazide (1.2 g, 7.8 mmol) and triethylamine (0.9 mL) in DMF (15 mL). The solution was stirred at 0° C. for 1 hour, and then stirred at room temperature for another hour. The hydrochloric salt of triethylamine was removed by filtration. The filtrate was added to distilled water. The desired product precipitated as white solids. The precipitate was filtered and dried in vacuum oven (0.7 g, yield 56%). $^1$H NMR (200 MHz, DMSO-d$_6$): δ 10.7 (s, 3H); 10.4 (s, 3H); 10.2 (s, 3H); 8.6 (s, 3H), 7.8 (d, 6H, J=8.0 Hz); 7.3 (d, 6H, 8.0 Hz) ppm; IR (KBr): 3249, 1657, 1608 cm$^{-1}$.

Example 5

Preparation of Ruthenium Complex Trimers VII

The synthesis and purification of VIII were performed in the same manner as described for ruthenium complex monomers IV in example 3. Their infrared characteristics are listed below.

VIII-a: IR (KBr): 3438, 1602, 1519, 1463, 842, 761 cm$^{-1}$.

VIII-b: IR (KBr): 1602, 1521, 844, 762 cm$^{-1}$.

VIII-c: IR (KBr): 3428, 1606, 842 cm$^{-1}$.

VIII-d: IR (KBr): 1516, 842, 761 cm$^{-1}$.

VII-e: IR (KBr): 1604, 1530, 843, 760 cm$^{-1}$.

Example 6

Preparation of Polymeric Ligands IX and X

Polymeric ligand IX-a:

Diethyl oxalate (1.46 g, 0.01 mol) was added to a stirred solution of the corresponding diamine (1.28 g, 0.011 mol) in DMF (20 mL). The reaction mixture was stirred at 60° C. for 5 hours. The prepolymer gradually precipitated from solution. The product was washed with methanol and dried under vacuum. The post-polymerization was carried out in a small tube under vacuum at 210° C. for 70 min. After the tube was cooled, trifluoroacetic acid was added to dissolve the resultant polymer, which was then was precipitated in methanol and washed with acetone.

Polymeric ligand IX-b:

A solution of oxalyl chloride (0.46 g, 3.6 mmol) in toluene (5 mL) was added to a stirred flask containing the corresponding diamine (3.05 g, 3.6 mmol), pyridine (0.6 mL) and toluene (20 mL) at room temperature. After being stirred at room temperature for 20 min, the reaction mixture was heated to 80° C. for 2 hours. After cooling down, the polymer was precipitated into methanol. The polymer product was collected by filtration and washed with acetone (2.2 g, 68% yield). IR (KBr): 3314, 2857, 1711, 1678, 1276 cm$^{-}$ $M_w$=8690 by GPC; $M_w/M_n$=1.74.

Polymeric ligand X-a: To 30 mL of NMP was added 1.74 g (0.01 mole) of adipic dihydrazide and 2.03 g (0.01 mole) of isophthaloyl chloride. The mixture was allowed to stir overnight at room temperature, under $N_2$, followed by precipitation of the product in 300 mL of vigorously stirred methanol. The product was isolated by filtration and dried overnight under vacuum. Yield was 2.6 g (69%).

Polymeric ligand X-b: Synthesis is the same as X-a, except using 1.74 g (0.01 mole) of adipic dihydrazide and 1.83 g (0.01 mole) of adipoyl chloride. Yield was 1.7 g (61%).

Polymeric ligand X-c: Synthesis is the same as X-a, except using 15 mL of NMP, 0.99 g (5 mmol) of isophthalic dihydrazide, 1.03 g (5 mmol) of isophthaloyl chloride. Yield was 1.4 g (69%).

Polymeric ligand X-d: To 15 mL of DMF, were added 523 mg (3 mmol) of adipic hydrazide and 505 mg (3 mmol) of 1,6-hexamethylene diisocyanate. The polymer, which precipitated from the reaction mixture, was isolated by filtration and dried overnight under vacuum. Yield was 0.8 g (78%).

Example 7

Preparation of Ruthenium Complex Polymers XI (Second Method)

A general procedure is given for the synthesis of XI-b as follows: Under an argon atmosphere silver trifluoromethanesulfonate (0.155 g, 0.60 mmol) was added into a solution of Ru(bpy)$_2$Cl$_2$.2H$_2$O (0.156 g, 0.3 mmol) in acetone (70 mL). The solution was stirred at room temperature for 2 hours. After filtration with a pad of Celite, the filtrate was evaporated to dryness. N,N-Dimethylformamide (10 mL) was added to the flask to dissolve the Ru(bpy)$_2$(acetone)$_2$(OTf)$_2$. The DMF solution of triflate salt was added into a solution of polymeric ligand IX-b (0.084 g, 0.095 mmol) and triethylamine (1 mmol) in DMF (10 mL). The reaction solution was heated to reflux for 3 hours under argon. After cooling to room temperature, 1 gram of ammonium hexafluorophosphate dissolved in 40 mL of water was added and a dark-red solid precipitated out of the solution. The ruthenium complex polymer XI-b was filtered off and washed with diethyl ether three times and dried under vacuum (5 mmHg). IR (KBr): 3411, 1658, 1604, 844 cm$^{-1}$.

Example 8

Preparation of Ruthenium Complex Polymers XII (First Method)

The synthesis and isolation were performed in the similar manner as described previously in examples 2 and 3.

XII-a: Using 200 mg (0.38 mmol) of Ru(bpy)$_2$Cl$_2$.2H$_2$O, 30 mg of polymeric ligand X-a and 100 mg of Na$_2$CO$_3$, yield was 230 mg (96%).

XII-b: Using 200 mg (0.38 mmol) of Ru(bpy)$_2$Cl$_2$.2H$_2$O, 35 mg of polymeric ligand X-b and 100 mg of Na$_2$CO$_3$, yield was 215 mg (90%).

XII-c: Using 200 mg (0.38 mmol) of Ru(bpy)$_2$Cl$_2$.2H$_2$O, 35 mg of polymeric ligand X-c and 100 mg of Na$_2$CO$_3$, yield was 218 mg (90%).

XII-d: Using 200 mg (0.38 mmol) of Ru(bpy)$_2$Cl$_2$.2H$_2$O, 33 mg of polymeric ligand X-d and 100 mg of Na$_2$CO$_3$, yield was 137 mg (56%).

Example 9

Preparation of Crosslinked Ruthenium Complex Films on ITO Electrode

The ruthenium complex trimer VIII-e (0.03 g, 0.0075 mmol) in 0.15 mL of acetonitrile is mixed at room temperature together with a triisocyanate (0.01 g, 0.011 mmol) in 0.1 mL of acetonitrile, as prepared from trimethylol propane and xylylene diisocyanate, followed by addition of 1,4-diazabicyclo[2,2,2]octane (4 mg) in 0.1 mL of acetonitrile. The prepolymer solution was then spin coated at a speed of 500–600 rpm onto an ITO electrode glass plate (ca. 2×2 cm). The resulting thin film was heated in an oven at 110° C. under a flow of argon for 2 hours. The cured films with a thickness about 360–420 nm were obtained and displayed the desired electrochromic property and switching profile, as shown in FIGS. 2 and 3.

REFERENCES

[1] B. Barber, C. R. Giles, V Askyuk, R. Ruel, L. Stulzl, D. Bishop, *IEEE Photonics Techno. Lett*, 10, 1262 (1998).
[2] T. Kawai, M. Koga, M. Okuno, T. Kitoh, *Electron. Lett.,* 34, 264 (1998).
[3] Y.-S. Jin, S.-S. Lee, Y.-S. Son, *Electron. Lett.,* 35, 916 (19998).
[4] (a) N. A. O'Brien, E. R. Mathew, B. P. Hichwa, *OFC* 1999, PD26-1. (b) M. A. Cowin, R. Varrazza, C. Morgan, R. V Penty, I. H. White, A. M. McDonagh, S. Bayly, J. Riley, M. D. Ward, J. A. McCleverty, *OFC* 2001, WR6-1.
(c) N. C. Harden, E. R. Humphrey, J. C. Jeffery, S. M. Lee, M. Marcaccio, J. A. McCleverty, L. H. Rees, M. D. Ward, *J. Chem. Soc., Dalton Trans.,* 2417 (1999).
[5] V Kasack, W. Kaim, H. Binder, J. Jordanov, E. Roth, *Inorg Chem.,* 34, 1924 (1995).
[6] B. Sullivan, D. Salmon, T. Meyer, *Inorg. Chem.* 17, 3334 (1978).

I claim:

1. A ruthenium complex having the formula

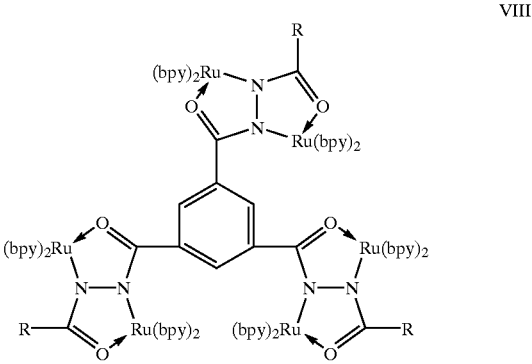

VIII where each of the R groups may be the same or different, and Is selected from the group consisting of hydrogen, alkyl, aryl, haloalkyl, hydroxyalkyl, NH$_2$, NR$_2$ with R$_2$ being alkyl or aryl.

2. A complex as set out in claim 1, in which at least one of R$_1$ and R$_2$ contains at least one other functional group selected from carboxylic acid (—COOH), hydroxyl (—OH), amino (—NH$_2$), acetylenic, alkenylenic and thio (—SH).

3. A complex as claimed in claim 1, in which each of the R groups is the same and is selected from the group consisting of:

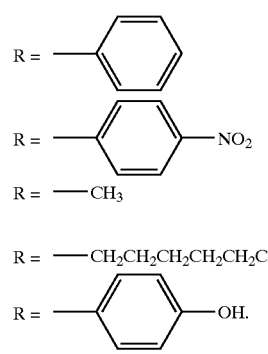

4. A complex polymer film, comprising a ruthenium complex of claim 1 crosslinked with a diisocyanate or a triisocyanate.

5. A complex polymer film, comprising a ruthenium complex of claim 1 crosslinked with a compound selected from (i) a diisocyanate selected from the group consisting of toluene diisocyanate, xylylene diisocyanate, hexahydroxylylene diisocyanate and hexamethylene diisocyanate and (ii) a triisocyanate prepared from trimetholyol propane and xylylene diisocyanate.

6. A light attenuating device comprising the complex of claim 1.

7. A light attenuating device comprising the complex polymer film of claim 5.

* * * * *